United States Patent
Berger et al.

(10) Patent No.: US 8,680,313 B1
(45) Date of Patent: Mar. 25, 2014

(54) SULFONATED AMPHOTERIC SURFACTANTS

(71) Applicants: Paul Daniel Berger, Sugar Land, TX (US); Christie Huimin Berger, Sugar Land, TX (US); Susanta Mohapatra, Sugar Land, TX (US)

(72) Inventors: Paul Daniel Berger, Sugar Land, TX (US); Christie Huimin Berger, Sugar Land, TX (US); Susanta Mohapatra, Sugar Land, TX (US)

(73) Assignee: Oil Chem Technologies, Inc, Sugar Land, TX (US)

( * ) Notice: Subject to any disclaimer, the term of this patent is extended or adjusted under 35 U.S.C. 154(b) by 0 days.

(21) Appl. No.: 13/998,107

(22) Filed: Oct. 1, 2013

(51) Int. Cl.
*C07C 309/02* (2006.01)

(52) U.S. Cl.
USPC ............................................................ 558/47

(58) Field of Classification Search
USPC ............................................................ 558/47
See application file for complete search history.

(56) References Cited

U.S. PATENT DOCUMENTS

| | | | |
|---|---|---|---|
| 5,371,250 | A | 12/1994 | Seitz et al. |
| 7,373,977 | B1 | 5/2008 | Berger et al. |
| 7,556,098 | B2 | 7/2009 | Berger et al. |

OTHER PUBLICATIONS

Ren and Luo Dynamic Interfacial Tension Behavior of Alkyl Amino Sulfonate in Crude Oil—Brine System—Tenside Surf. Del 50 (2013) 5 p. 369-375.

*Primary Examiner* — Kristin Vajda

(57) ABSTRACT

Sulfonated betaines, amine oxides, and sultaines are made by the reaction of the corresponding unsaturated betaines, amine oxides or sultaines with a sulfonating agent. These amphoteric surfactants have demonstrated low adsorption properties in addition to good compatibility with brine containing high concentrations of salt and divalent cations. They can be employed in applications where their respective conventional amphoteric surfactants are used including: personal care, mining, improved oil recovery (IOR), oil field drilling, fracturing, acidizing, foaming, and agricultural formulations.

1 Claim, No Drawings

SULFONATED AMPHOTERIC SURFACTANTS

FIELD OF INVENTION

The present invention discloses the composition and method of synthesis of certain amphoteric sulfonated betaines, amine oxides, sulfobetaines, and sultaines. This patent application has been filed simultaneously with a patent application for the use of these sulfonated amphoteric surfactants in Oil Field and Improved Oil Recovery.

BACKGROUND AND DESCRIPTION OF PRIOR ART

Amphoteric surfactants have been used for many applications including personal care, mining, improved oil recovery (IOR), oil field drilling, fracturing, acidizing, foaming, and agricultural formulations, etc. because of their unique properties such as electrolyte tolerance, hard water tolerance, mildness and low irritation, foaming, wetting, interfacial tension reduction, viscoelasticity, and thermal stability. U.S. Pat. No. 7,373,977 discloses the use of certain amidopropyl dimethyl betaines and alkyl dimethyl betaines as viscoelastic surfactants for oil well stimulations. U.S. Pat. No. 7,556,098 discloses the use of certain unsaturated amidopropyl dimethyl betaine, alkyldimethyl betaines, amidopropyl dimethyl sultaines, and alkyl dimethyl sultaines to lower interfacial tension (IFT) to ultralow values for the recovery of residual oil. However, for oil field applications, one of the shortcomings of these products is their high adsorption to solid surfaces. The high adsorption of the amphoteric surfactants onto the formation rock prevents the surfactant from propagating through the reservoir and the oil recovery is limited. It would be very valuable if an amphoteric surfactant or surfactants could be developed having all the desired properties of existing amphoteric surfactants with low adsorption onto the solid phase.

U.S. Pat. No. 5,371,250 describes a method of preparing pure aqueous betaines by reacting tertiary amines with an α-monohalocarboxylic acid, and an alkali metal hydroxide in the presence of water to make the betaine. The aqueous betaine solution is then treated with a sulfonating agent to convert the alpha-monohalocarboxylic acid into the corresponding sulfocarboxylic acid to make the highly pure aqueous betaine solution of the formula.

A recent article, Dynamic Interfacial Tension Behavior of Alkyl Amino Sulfonate in Crude Oil-Brine System, Tenside Surf. Det. 50 (2013) 5 pages 369-375 describes the interfacial tension behavior of alkyl amino sulfonate. Although the IFT of these surfactants may achieve ultra low values with certain oil and brines, the challenges of the surfactants are the adsorption rate onto the rock. In addition these surfactants are anionic in nature and it is well known in the industry that anionic surfactants are subjected to limited compatibility in brines containing divalent cations. It would be very valuable if a surfactant can provide low adsorption properties onto the rock, compatibility with the various brine composition, low IFT between the injection fluid and oil, stability at higher temperature, and effectively recovery the residual oil.

BRIEF DESCRIPTION OF THE INVENTION

The invention discloses the composition and method of synthesis of various sulfonated amphoteric surfactants including but not limited to, alkyl amido betaine sulfonates, alkyl betaine sulfonates, alkyl hydroxyl sultaine sulfonates, alkyl amido hydroxysultaine sulfonates, alkyl sulfobetaine sulfonates, alkyl amido sulfobetaine sulfonates, alkyl amine oxide sulfonates, and alkyl amido amine oxide sulfonates. The present invention involves using a sulfonating agent to react with the double bond of unsaturated amphoteric surfactants, to produce the sulfonated amphoteric surfactants. These sulfonated amphoteric surfactants have been found to give low adsorption onto reservoir rock, ultra-low (IFT, viscoelastic properties, compatibility with brines containing high salt and divalent ions, and are stable at higher temperature.

DETAILED DESCRIPTION OF THE INVENTION

The present invention involves the sulfonation of amphoteric surfactants, including but are not limited to alkylene betaines, alkylene amidopropyl betaines, alkylene dimethyl betaine, alkylene hydroxyl sultaines, alkylene sulfobetaine, alkylene amine oxide, alkylene amidopropyl amine oxides, alkylene amidoalkylsultaines, and alkylene sultaines. The reaction shown below is an example of sulfonation with sodium meta-bisulfite. The unsaturated amphoteric surfactants are sulfonated by methods known to the art including but not limited to falling film sulfur trioxide sulfonation, meta-bisulfite sulfonation, chloro sulfonic acid sulfonation, sulfamic acid sulfonation, cold SO2/SO3 sulfonation. In cases where sulfonic acids are formed, for example using sulfur trioxide, the product is neutralized to form a salt.

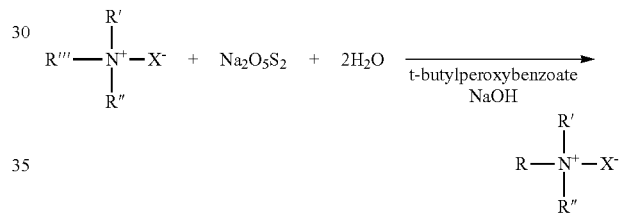

Where

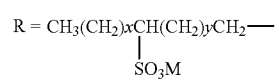

or

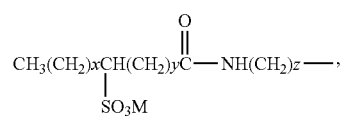

R'=C1-C6 alkyl,
R"=C1-C6 alkyl or

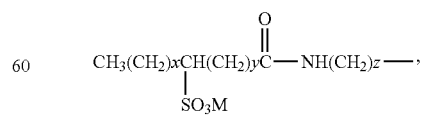

R'''=CH3(CH2)xC=C(CH2)y— or $CH_3(CH_2)xCH=CH(CH_2)yCH-NH(CH_2)z-$,
X=$(CH_2)aCOO$ or, $CH_2CH(OH)CH_2SO_3$ or, $(CH_2)bSO_3$, or O, x=4-28,
y=4-28,
z=1-6,
a=1-3,
b=1-6,
M=mono or divalent metal cation or ammonium cation.

Unsaturated R groups (alkylene groups) include but are not restricted to palmitoleyl, myristoleyl, oleyl, erucyl, nervonyl. They may be present individually or as mixtures of two or more as found naturally or synthetically blended.

The reaction to synthesize the unsaturated amphoteric surfactants is carried out between about 50° C. and 110° C. with about 80° C. being preferred in most cases. Any free radical catalyst known to the art can be used to initiate and accelerate the addition of the sulfonate group to the double bond. The pH can be adjusted during the reaction with organic bases such as amines as well as inorganic bases such as sodium hydroxide or sodium carbonate.

EXAMPLES

Example 1

Synthesis of Erucyl Dimethyl Betaine Sulfonate

Procedure: A solution was made by mixing 8.4 g Na-metabisulfite (0.0419 Moles) and 2 g NaOH (0.0419 Moles) in 20 g distilled water at 22° C. in a three necked glass flask until uniform. 100 g (0.075 moles) erucyl dimethyl betaine was added to this solution at 22° C. The solution was heated to 75° C. and. 3 g tert-butylperoxybenzoate was added dropwise as the catalyst while contining to mix. The reaction was monitored by the 2-phase titration using sodium lauryl sulfate and Hyamine. 62% conversion was obtained after 8 hours reaction.

Example 2

Synthesis of Erucyl Dimethyl Hydroxyl Sultaine Sulfonate 24.2 g (0.01815 mol) erucyl dimethyl sultaine was added to a three necked glass flask. One gram 50% NaOH solution was added while mixing and gradually heating to 80° C. 4.71 g sodium metabisulfite (0.0235 mol) was added to the erucyl dimethyl sultaine solution. 3 g tert-butylperoxybenzoate was added dropwise. The reaction was monitored by two phase titration using sodium lauryl sulfate. A complete conversion was achieved in 6 hours. Unlike erucyl dimethyl hydroxy sultaines, erucyl dimethyl hydroxy sultaine sulfonate is viscoelastic and low adsorbing on to sandstone.

Example 3

Synthesis of Amine Oxide Sultaine

A solution of oleyl amine oxide (30 g, 0.0921 mol) was made in 20 g distilled water at 80° C. and added to a three-necked flask. Another solution of sodium metabisulfite (8 g, 0.04 mol) was made in 10 g distilled water at 22° C. To the amine oxide solution, sodium metabisulfite solution and tert-butylperoxybenzoate (5 g) were added simultaneously and mixed. The temperature was brought back up and maintained at 80° C. The reaction was monitored by back titration using sodium lauryl sulfate and Hyamine. A complete conversion was achieved in 9 hours. The product is soluble in brine at 22° C. On the other hand, the oleyl amine oxide is not soluble in brine at 22° C. but only soluble above 60° C.

The invention and the manner and process of making and using it, have been described in such full, clear, concise, and exact terms as to enable and person skilled in the art to which it pertains, to make and use same. It is to be understood that the foregoing describes preferred embodiments of the present invention and that modifications may be made therein depending from the spirit and scope of the present invention as set for the in the claims.

The invention claimed is:

1. A composition of amphoteric surfactants of the structure

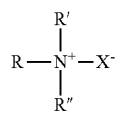

Where

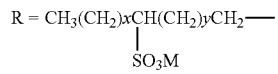

or

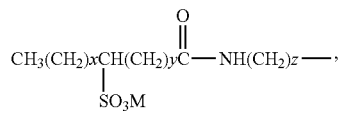

R'=C1-C6 alkyl,
R"=C1-C6 alkyl or,

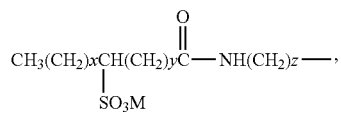

X=$(CH_2)_aCOO$ or $CH_2CH(OH)CH_2SO_3$ or $(CH_2)_bSO_3$ or O,
x=4-28,
y=4-28,
z=1-6,
a=1-3,
b=1-6, and
M=mono or divalent metal cation or ammonium cation.

* * * * *